United States Patent
Schaefer et al.

(10) Patent No.: US 8,858,580 B2
(45) Date of Patent: *Oct. 14, 2014

(54) TONGUE CLEANING DEVICE

(75) Inventors: Norbert Schaefer, Frankfurt am Main (DE); Vladimir Gartstein, Mason, OH (US); Donald James White, Jr., Fairfield, OH (US)

(73) Assignee: Braun GmbH, Kronberg (DE)

( * ) Notice: Subject to any disclaimer, the term of this patent is extended or adjusted under 35 U.S.C. 154(b) by 238 days.

This patent is subject to a terminal disclaimer.

(21) Appl. No.: 13/099,531

(22) Filed: May 3, 2011

(65) Prior Publication Data

US 2011/0289707 A1    Dec. 1, 2011

Related U.S. Application Data

(60) Provisional application No. 61/331,969, filed on May 6, 2010.

(51) Int. Cl.
| | | |
|---|---|---|
| *A61B 17/24* | (2006.01) | |
| *A46B 15/00* | (2006.01) | |
| *A61N 1/32* | (2006.01) | |
| *A61N 1/05* | (2006.01) | |
| *A61B 17/00* | (2006.01) | |
| *A61B 19/00* | (2006.01) | |

(52) U.S. Cl.
CPC ........... *A61B 17/244* (2013.01); *A46B 15/0081* (2013.01); *A61B 2017/00734* (2013.01); *A61B 2017/00398* (2013.01); *A61N 1/322* (2013.01); *A61N 1/0548* (2013.01); *A61B 19/5202* (2013.01); *A46B 15/0022* (2013.01); *A46B 15/0002* (2013.01)
USPC ........................................... 606/161; 606/41

(58) Field of Classification Search
CPC ...................................................... A61B 17/244
USPC ............ 15/106, 111, 236.01; 606/32, 41, 161
See application file for complete search history.

(56) References Cited

U.S. PATENT DOCUMENTS

| | | | | |
|---|---|---|---|---|
| 5,133,102 | A | * | 7/1992 | Sakuma ........................ 15/167.1 |
| 5,372,501 | A | * | 12/1994 | Shalvi ............................. 433/32 |
| 6,056,763 | A | | 5/2000 | Parsons |
| 6,102,923 | A | | 8/2000 | Murayama |
| 8,201,298 | B2 | * | 6/2012 | Hohlbein ......................... 15/110 |
| 2005/0000049 | A1 | | 1/2005 | Hohlbein |
| 2006/0010628 | A1 | * | 1/2006 | Moskovich ...................... 15/111 |
| 2006/0070195 | A1 | * | 4/2006 | Morita et al. .................... 15/105 |
| 2007/0212665 | A1 | | 9/2007 | Jimenez et al. |
| 2009/0198262 | A1 | | 8/2009 | Rosenblood et al. |

FOREIGN PATENT DOCUMENTS

WO    WO02071967 A2    9/2002

OTHER PUBLICATIONS

International Search Report and written opinion, mail date Jul. 8, 2011, 11 pages.

\* cited by examiner

*Primary Examiner* — Kathleen Holwerda
*Assistant Examiner* — Sarah W Aleman
(74) *Attorney, Agent, or Firm* — Vladimir Vitenberg

(57) ABSTRACT

A head portion for a tongue cleaning device is disclosed. The head portion includes a mechanical tongue cleaning section and a tongue cleaning electrode. The mechanical tongue cleaning section includes a cleaning protrusion. The tongue cleaning electrode enables a current flow into a user's tongue during operation.

31 Claims, 13 Drawing Sheets

TONGUE CLEANING DEVICE

CROSS REFERENCE TO RELATED APPLICATION

This application claims the benefit of U.S. Provisional Application No. 61/331,969, filed May 6, 2010, the substance of which is incorporated by reference in its entirety herein.

FIELD OF THE INVENTION

The present disclosure relates to a head portion of a tongue cleaning device comprising a mechanical tongue cleaning section having at least one protrusion. More particularly, the present disclosure further relates to a tongue cleaning device comprising a head portion having a mechanical tongue cleaning section having at least one protrusion.

BACKGROUND OF THE INVENTION

Halitosis or most commonly bad breath is the result of contamination of the tongue by mostly anaerobic bacteria. When left on the tongue the anaerobic respiration of those bacteria can yield a plurality of bad smells. In order to fight malodour from the tongue it is necessary to remove the bacteria from the tongue. Mints, mouth sprays, mouth wash or gum usually only provide temporary relief as the tongue surface is very rough and the bacteria can hide in the pits and fissures. In order to provide a better cleaning, tongue cleaners or tongue scrapers are known for collecting and removing the bacterial coating of the tongue. Ergonomic tongue cleaners are shaped in accordance with the anatomy of the tongue, and are optimized to lift and trap the plaque coating and effectively clean the surface of the tongue. There are many different types and designs of tongue cleaners made from plastic, metal or other materials. Most tongue cleaners can generally be described as being spoon-shaped comprising a head portion and a handle portion while having plurality of nibs at their head portion facing towards the tongue for scrubbing the tongue when in operation.

Still the problem remains that a substantial portion of the bacteria stay in the pits and fissures between the papillae of the tongue spreading malodour even after tongue cleaning with known tongue cleaners.

SUMMARY OF THE INVENTION

In one embodiment, a head portion for a tongue cleaning device is provided. The head portion includes a mechanical tongue cleaning section and a tongue cleaning electrode. The mechanical tongue cleaning section includes a cleaning protrusion. The tongue cleaning electrode enables a current flow into a user's tongue during operation.

In another embodiment, a tongue cleaning device is provided. The tongue cleaning device includes a head portion having a mechanical tongue cleaning section; and a tongue cleaning electrode for enabling a current flow into a user's tongue during operation. The device further includes a handle portion, a contact electrode enabling a current flow into a user's body in a use state, and an energy source. The energy source is electrically connected to the contact electrode and to the tongue cleaning electrode such that in a use state a current flow is enabled between the contact electrode and the tongue cleaning electrode through a user's body.

In another embodiment, a method for cleaning a human or animal tongue is provided. The method includes the steps of: providing an ionic antibacterial agent in proximity to the tongue, providing an electrical current flow from a first electrode to and through the tongue, wherein the current flow is at least partly provided by the ionic antibacterial agent. The method further comprises the step of mechanically scrubbing the tongue, wherein it is preferable if this step is carried out simultaneously to providing the current flow.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
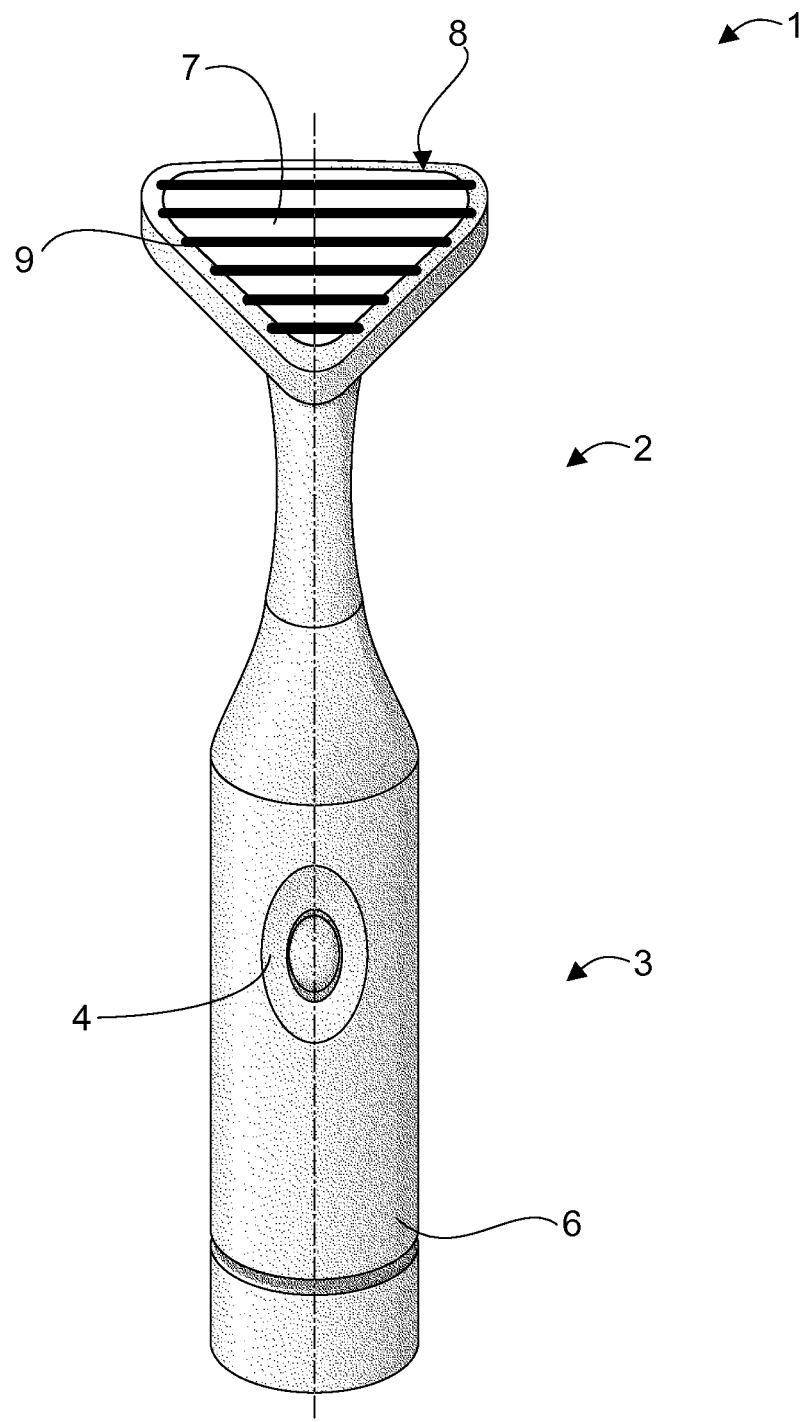
FIG. 1 is a frontal view of a first exemplary embodiment of a tongue cleaning device.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, it is desirable to provide a tongue cleaning device enabling a more effective cleaning of the tongue. This desire is satisfied by a head portion of a tongue cleaning device in accordance with the present disclosure.

According to one embodiment, a tongue cleaning device or the respective head portion as disclosed includes a mechanical tongue cleaning section having at least one cleaning protrusion and a tongue cleaning electrode enabling a current flow into a user's tongue when in use. The head portion of a tongue cleaning device according to the present disclosure not only enables a mechanical scrubbing of the tongue but also an electrically driven cleaning process based on electrophoresis.

According to one embodiment, a tongue cleaning device includes a head portion and further a handle portion having a contact electrode, wherein the contact electrode enables a current flow via the user's body (typically the hand, but the current flow may go via the lips of the user, depending on the location of the contact electrode) when in use, and an energy source, wherein the energy source is electrically coupled to the contact electrode and to the tongue cleaning electrode such that in operation a current may flow from the electrode in the handle portion through a user's body to the electrode in the head portion or vice versa.

The term "electrically coupled" as used herein should encompass embodiments where a selection element, for example, an on/off-button, is present in the electrical coupling to selectively switch the electrical coupling on or off. The arrangement of contact electrode in the handle portion and tongue cleaning in the head portion allows for providing a current flow from one of the electrodes to the other through the user's body. The bacteria on the tongue may be treated with anti-bacterial agents comprising ions having anti-bacterial properties when brought into contact with the bacteria. The anti-bacterial agents can be provided for example in a cleaning substance like a dentifrice or a rinse which is applied into the user's mouth.

In an embodiment, the cleaning substance or anti-bacterial agents may be provided as an integral part of the tongue cleaning device, for example in a gel cushion located close to the tongue cleaning electrode. In another embodiment, the bacteria may be attacked by ionised water without addition of an anti-bacterial substance. In another embodiment, the tongue cleaning electrode may itself provide anti-bacterial ions, for example, when the tongue cleaning electrode is made from silver or a silver containing alloy. The combined mechanical scrubbing together with the effective transport of anti-bacterial ions to the bacteria allows for an effectively improved cleaning of the tongue.

In an embodiment, the surface of the tongue cleaning electrode contacting the tongue and the mechanical tongue cleaning section are located on the same side of the head portion such that their surface normals are at least partly facing into the same direction, i.e. towards the tongue when in use. In other words, the tongue cleaning electrode and the mechanical tongue cleaning section are arranged such that they simultaneously get in contact with the user's tongue.

The polarity of the applied current will of course depend on the charging of the anti-bacterial agent in order to provide an effective flow of the anti-bacterial agent into the pits and fissures of the tongue. When, for example, positively charged ions (cations) are used, then the tongue cleaning electrode must be positively charged (against the contact electrode) to provide effective driving of the cations towards the tongue. The current strengths and polarity may be manually adjustable by the user, for example, by one or several control elements provided at the tongue cleaning device. The current strengths can be reduced to allow the user to become acquainted to the device and later to choose the optimal strengths. If a user is very sensitive at the tongue it is thus possible to reduce the current strengths or if a user suffers from strong malodour a higher strengths of current can be used.

In an embodiment, the applied current is a constant DC current. Alternatively an AC current or a pulsed current may be used in order to optimize a tongue cleaning. In another embodiment, a periodic change of the polarity of a DC current may be used. In order to restrict the current through the user's body to a physiologically harmless or for the user comfortable level the energy source may be arranged such that it limits the current. In an embodiment, the current provided by the energy source through the user's body is in a range of from about 20 µA to about 700 µA and in another embodiment between about 50 µA and about 400 µA. In the experience of the inventors, levels over about 80 µA appear to produce unpleasant sensations in users, an electrical feeling and/or sour tastes and in somce cases pain. However, the application of increased ionic current levels may be desirable to increase the efficacy of such tongue cleaning devices. Accordingly, tongue cleaning devices that enable increased ionic microcurrent levels without causing unpleasant sensations in users of such devices and methods are desired. For example, a ramping current control that increases the level of microcurrent from a start current to an end current over a period of time may be used.

In one embodiment, the voltage difference applied between the electrodes ranges from about 8 Volts to about 20 Volts. In particular the applied voltage difference has a value of 8 Volts, 10 Volts, 12 Volts, 14 Volts, 16 Volts, 18 Volts or 20 Volts. In a further embodiment, the tongue cleaning electrode is a laminar electrode. Here, the term "laminar" means that the tongue cleaning electrode is non-structured. It shall not exclude that the tongue cleaning electrode has a curvature, for example, to adapt to the outer surface of the tongue cleaning device.

In an embodiment, the area over which the mechanical tongue cleaning section extends at least partly spatially overlaps with the area over which the tongue cleaning electrode extends. This guarantees that when mechanically scrubbing the tongue with the mechanical tongue cleaning section of the head portion an electric current can be applied to the tongue for simultaneously enabling the above described cleaning process by electrophoresis. In a further embodiment, the areas of the mechanical cleaning section and of the tongue cleaning electrode on the head portion are identical and overlap to full extend.

In another embodiment, the mechanical tongue cleaning section comprises a plurality of cleaning protrusions. Those cleaning protrusions may have various designs for enabling an effective scrubbing of the tongue in order to mechanically remove bacteria from the tongue. The cleaning protrusions may have the shape of ribs or nubs, but this shall not exclude the use of any other shapes. For purposes herein, the term cleaning protrusion shall exclude filaments, for example filaments used as bristles in a tooth brush. A filament if compared to a cleaning protrusion according to the definition used herein has an additional degree of freedom for flexing. A cleaning protrusion on the other hand has the function of following the motion of the carrier and to transmit a significant force for efficient scrapping of the tongue. For the particular application of the present disclosure a significant bending would be disturbing the functionality. A cleaning protrusion in the sense of the present disclosure follows the motion of the carrier and allows no or only little internal flexing.

Filaments in toothbrushes made out of Nylon or other plastic materials have typically natural harmonics of from about 400 to about 800 Hz. Those can be calculated by the well known formula:

$$\omega_0 = \sqrt{\frac{E \cdot I \cdot k}{\rho \cdot A \cdot L}},$$

wherein E is the Young Modulus, I is the second moment of area of the cross section, k is the form factor describing the boundary conditions as fixed and free oscillating, ρ is the density, A is the cross sectional area of the filament and L is the length of the filament (or beam). Natural frequencies for complex structures with an uneven diameter can be calculated with finite element modelling methods.

A cleaning protrusion typically does not allow any significant movement within itself and therefore does have significantly higher natural frequencies than a filament. A cleaning protrusion as used herein shall have a natural frequency of more than about 1200 Hz, in another embodiment more than about 2000 Hz and in yet another embodiment more than about 3000 Hz. In a further embodiment, the natural frequency of a cleaning protrusion is equal to or larger than about 4000 Hz and in another embodiment, more than about 5000 Hz. This high natural frequency results in an internal stiffness that is so high that it would follow the motion of the carrier without any noticeable flexing.

For example a cylindrical cleaning protrusion formed of nylon with a length of 5 mm, a diameter of 0.15 mm and a Young modulus of 3000 N/mm² treated as a cylindrical beam with one end fixed and the other end freely oscillating does have a natural frequency of 1400 Hz. At a length of 2.5 mm it would be 5690 Hz.

In an embodiment, the cleaning protrusion is formed of an elastomeric plastic material. In some embodiments, the cleaning protrusion is made of electrically isolating material. The cleaning protrusion may extend over the width of the tongue cleaning electrode. Then, the cleaning protrusion acts as a spacer element between the tongue cleaning electrode and the user's tongue, thus it at least partly avoids direct contact between the tongue cleaning electrode and the tongue.

In a further embodiment, the tongue cleaning electrode is realized as a laminar electrode partly covered by a plurality of electrically isolating cleaning protrusions, for example, formed like ribs. When viewed from above the cleaning protrusions of the mechanical tongue cleaning section form a grid. In an embodiment, the tongue cleaning electrode comprises a material selected from a group consisting of metal, in particular noble metal, for example, silver, stainless steel, an electrically conductive plastic or a combination thereof.

In another embodiment, the tongue cleaning electrode may be structured to itself form at least a part of the mechanical tongue cleaning section. This may for example be realized by structuring the tongue cleaning electrode, for example, using an etching process or a stamping process. In such an embodiment, the tongue cleaning electrode fulfils a double functionality, namely to provide a conductive surface coupled to an energy source so that an electric contact with the tongue can be established during operation and to provide a structure that acts as a cleaning protrusion for mechanically cleaning the tongue. It shall not be excluded that additional cleaning protrusions are provided by the mechanical tongue cleaning section that are made from an isolating material.

In another embodiment, the tongue cleaning electrode comprises a plurality of cleaning protrusions in the form of nubs. These nubs pointing towards the user's tongue to provide places of high current density assisting to drive the ions as deep as possible into the pits and fissures between the papillae in addition to their function to work as mechanical cleaning elements. While the plurality of nubs may be formed from a single piece of electrically conductive material, for example, by punching a sheet of metal foil, the nubs need not necessarily be manufactured of a single piece, but could for example be arranged as a set of individual balls, which are separated from each other. In an embodiment, the cleaning protrusions, in particular being in the form of nubs, have a height in a range from about 0.1 mm to about 2 mm measured from the level of the material surrounding the nub.

A nub in the sense of the present disclosure is a protrusion whose height above the surrounding material is larger than or about equal to its width (or diameter). The nubs may have all kinds of different shapes. In particular, the nubs may be cylindrical, conical or (hemi-)spherical. Beside nubs having a circular base area it is of course possible to have nubs having a triangular, rectangular or any other base area. The nubs may be arranged in a particular pattern or alternatively they could be arranged randomly. In one embodiment, the cleaning protrusions, in particular being in the form of nubs, have a width in a range from about 0.1 mm to about 3.0 mm. In another embodiment in which the nubs have a circular cross-section, the widths of the nub is identical to its diameter. In a further embodiment, the height of the cleaning protrusions, in particular the height of the nubs, is less than five times their diameter or width.

In an embodiment, the area of the tongue cleaning electrode covered by the cleaning protrusions is in a range from about 1% to about 50% of the overall area of the tongue cleaning electrode. In an embodiment, the area of the tongue cleaning electrode covered by the nubs is in a range from about 1 mm² to about 100 mm². In a further embodiment, the current density at the electrically conductive sections of the tongue cleaning electrode is higher than about 0.5 µA/mm² and less than about 60 µA/mm². For example for a current of 100 µA, the area of the electrically conductive sections of the electrode must have an area of less than about 200 mm². In an embodiment, the high current density at the nubs is achieved when the nubs have a density of between about 5 nubs/cm² and about 50 nubs/cm².

The current density at the tip of each nub is even further enhanced when the electrically conductive nubs of the tongue cleaning electrode are separated from each other by electrically isolating material sections. This may in an embodiment be achieved by first forming an electrically conductive electrode comprising the nubs while in a second step the spacing between the nubs is partly filled with an electrically isolating material. The nubs may still protrude over the electrically isolating material. In an embodiment, the overall area of the electrically conductive sections of the tongue cleaning electrode is smaller than about 200 mm² and in another embodiment equal to about 150 mm² or less.

In another embodiment, the ratio between the area of the tongue cleaning electrode covered by the cleaning protrusions and the overall area of the electrode is equal to or less than about 0.7, in another embodiment equal to or less than about 0.3 and in yet another embodiment, in a range of between about 0.1 and about 0.3. The tongue cleaning electrode may have a width in a range of between about 0.2 cm and about 6 cm and in another embodiment in a range of between about 0.5 cm and about 3 cm.

As the head portion of the tongue cleaning device shall fit into the user's mouth, the overall height of the head portion in the section where the mechanical tongue cleaning section and the tongue cleaning electrode are located is smaller than about 15 mm and in another embodiment smaller than about 10 mm. In an embodiment, the head portion comprises an emitter for electromagnetic radiation, in particular a light emitting diode. This emitter may emit light in the visible range for illuminating the user's mouth. However, in other embodiments emission in other ranges of the electromagnetic spectrum may be implemented.

In an embodiment, the head portion and the handle portion are detachably mounted to each other such that the head portion may be realized as a disposable replacement part. In order to achieve this it may be useful if the head portion and/or the handle portion include a mechanical connector for establishing a mechanical connection between the head portion and the handle portion and/or an electrical connector between the head portion and the handle portion in order to establish an electrical connection. The electric current flowing through the user's body will be substantially reduced when a current flow is provided between the tongue cleaning electrode and the contact electrode, for example, by a water film extending from the head portion to the handle portion. In order to prevent build-up of an electrically conductive film between the two electrodes, the head portion and/or the handle portion may comprise a protrusion, for example an annular protrusion, acting as a tear-off edge for the film.

It is also contemplated that the tongue cleaning device further comprises a plurality of cleaning elements on the head portion (for example, bristles or elastomeric elements) for cleaning teeth, which could be arranged on a side of the head portion opposite to the tongue cleaning electrode such that the cleaning elements and the tongue cleaning electrode would not simultaneously get into contact with the user's tongue. In another embodiment, cleaning elements such as bristles are provided in proximity of the tongue cleaning electrode and the mechanical tongue cleaning section to enhance the tongue cleaning performance.

In an embodiment, the tongue cleaning device, in particular the head portion and/or the handle portion are arranged such that they provide for a vibration of the head portion, in particular of the mechanical tongue cleaning section. Such a vibration could, for example, be caused by an ultrasound device (for example, a piezoelectric vibrator) integrated into the head section of the handle section or by including a motorized eccentric mass on an axis.

In another embodiment, the head portion may be attachable to a known handle portion having no contact electrode. The head portion could then be realized as a replacement head for a standard toothbrush handle. In this case the head portion could comprise a contact electrode to be touched by the user's hand or the user's lips in order to establish a current flow through the user's body at the end proximal the handle portion. In order to provide a current flow the head portion in such an embodiment could also comprise an energy source, in particular a battery (for example, a coin cell) or rechargeable battery.

Figure 2:
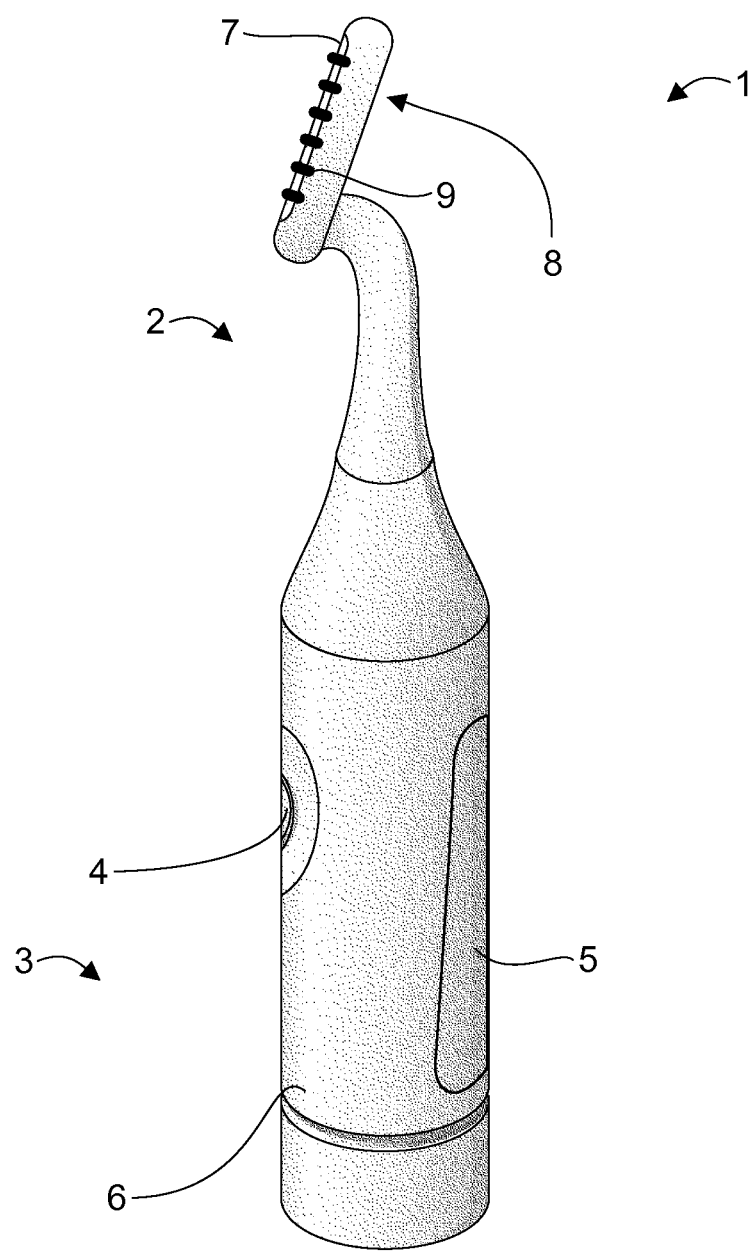
FIG. 2 shows a side view of the tongue cleaning device shown in FIG. 1.

FIGS. 1 and 2 show a first exemplary embodiment of a tongue cleaning device 1. The tongue cleaning device 1 comprises a head portion 2 and a handle portion 3. In the depicted first embodiment, the head portion 2 and the handle portion 3 form an integral device, but the head portion 2 may be arranged as a detachable part to enable easy replacement of the head portion 2. The handle portion 3 comprises an energy source, for example, a rechargeable battery, for providing a supply voltage for driving a current flow initiating the transport of anti-bacterial agents into the user's tongue in an operation state, as will be explained further below. The handle portion 3 further comprises an on/off-switch button 4 and a contact electrode 5 placed on the rear side of the cylindrical housing of the handle portion 3 for establishing a contact between the contact electrode 5 and a user's hand during operation. Here, the contact electrode 5 is formed integrally with a housing 6 of the handle portion 3 by injection molding an electrically conductive plastic material in a two-component or multi-component injection molding process. The contact electrode 5 is electrically coupled to the energy source. When the handle portion 3 is held by the user's hand, the contact electrode 5 is in direct contact with the user's hand, thus establishing a first electrical connection to the user's body.

The head portion 2 comprises a tongue cleaning electrode 7 as well as a mechanical tongue cleaning section 8. In the shown first embodiment, the tongue cleaning electrode 7 and the mechanical tongue cleaning section 8 of the head portion 2 extend approximately over the same area while the mechanical tongue cleaning section 8 is arranged above (with respect to the tongue of the user; this means that the mechanical tongue cleaning section is closer to the user's tongue when in operation) the tongue cleaning electrode 7.

In the first embodiment depicted in FIGS. 1 and 2, the tongue cleaning electrode 7 is made from an electrically conductive metal sheet forming part of the outer surface of the head portion 2 and thus provides an electric contact to parts of the user's oral cavity, in particular to its tongue, which is the intended use. In this first embodiment, the mechanical tongue cleaning section 8 is formed by a plurality of cleaning protrusions in the form of six ribs 9 that each extend over the tongue cleaning electrode 7 for mechanically scrubbing the user's tongue. The ribs are made from an elastomeric plastic material and have an extension direction essentially perpendicular to the symmetry axis (or: longitudinal axis) of the essentially cylindrical handle section 3.

When in use the device 1 is inserted into the user's oral cavity and the head portion 2 is brought into contact with the user's tongue. In operation the side of the head portion 2 carrying the tongue cleaning electrode 7 and the mechanical cleaning section 8 is facing towards the user's tongue. The device 1 is moved such that the ribs 9 scrub over the surface of the tongue in order to mechanically remove part of the malodour producing bacteria. In addition to the mechanical cleaning, the tongue cleaning device 1 is electrically switched on by actuating the on/off-button 4. When switched on the energy source inside the handle portion 3 provides a voltage to the contact electrode 5 in the handle portion 3 as well as to the tongue cleaning electrode 7 in the head portion 2 such that a voltage difference pertains between the both electrodes.

Assuming that the device 1 is inserted into the user's oral cavity by holding the handle portion 3 in the user's hand a current starts to flow through the user's body from the tongue cleaning electrode 7 to the contact electrode 5 in the handle portion 3 or vice versa as soon as the tongue cleaning electrode 7 is brought into contact with the tongue and a conductive connection is established, typically via saliva that may additionally comprise dentifrice or mouth rinse etc.

For the present example it is assumed that the user has inserted a cleaning agent (for example, a cleaning liquid) into the mouth containing positively charged ions before inserting the tongue cleaning device 1 into the oral cavity. The cleaning agent has anti-bacterial properties. To achieve optimal results for driving the anti-bacterial ions into the pits and fissures between the papillae of the tongue the voltage is applied to the tongue cleaning electrodes 7 and the contact electrode 5 such that the tongue cleaning electrode 7 is positively charged against the contact electrode 5.

Figure 3:
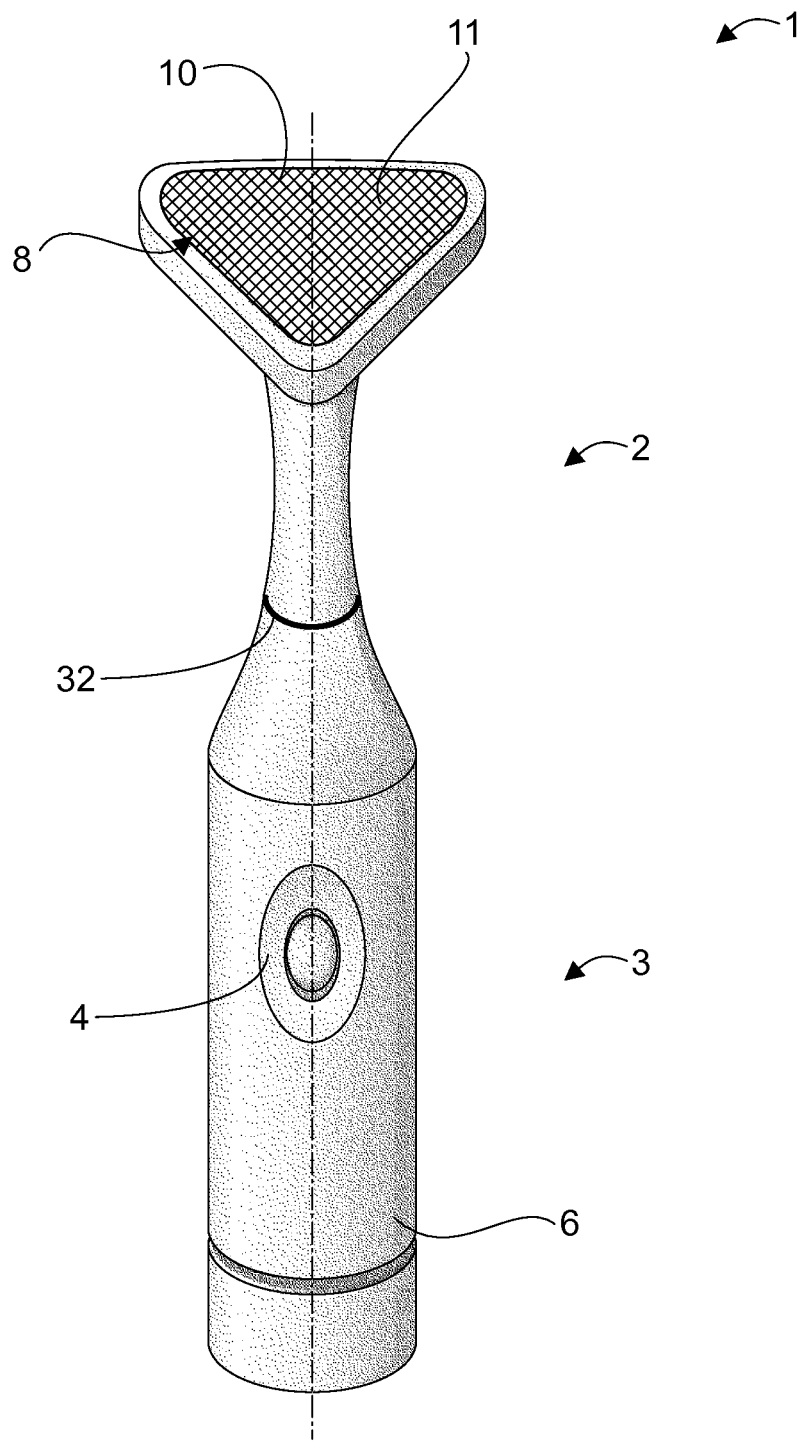
FIG. 3 is a frontal view of a second exemplary embodiment of a tongue cleaning device.

FIG. 3 shows an alternative second exemplary embodiment of a tongue cleaning device 1. The plane and non-structured tongue cleaning electrode 7 as well as the ribs 9 of the mechanical tongue cleaning section 8 shown in FIGS. 1 and 2 have been replaced by a single laterally extending tongue cleaning electrode 10. The tongue cleaning electrode 10 of this second embodiment not only provides the functionality of a tongue cleaning electrode, but simultaneously forms the mechanical tongue cleaning section 8. In order to fulfill both functionalities, the tongue cleaning electrode 10 has a structured surface formed by etching a set of perpendicularly arranged grooves 11 into the tongue cleaning electrode 10. By applying the grooves 11 into the tongue cleaning electrode 10 the surface of the tongue cleaning electrode 10 consists of a more or less regular structure of cleaning protrusions in the form of rhombi extending above the grounds of the grooves 11. The arrangement of rhombi on the surface of the tongue cleaning electrode 10 serves the same purpose of mechanically scrubbing over the user's tongue when the device is in use as the ribs 9 of the device depicted in FIGS. 1 and 2, namely to provide cleaning protrusions.

In the second embodiment depicted in FIG. 3, the head portion and the handle portion can be separated from each other at the mechanical and electrical interface 32, i.e. the tongue cleaning device 1 is a two part device having a detachable head portion 2, which may be a disposable head portion to be replaced when it is worn out.

Figure 4:
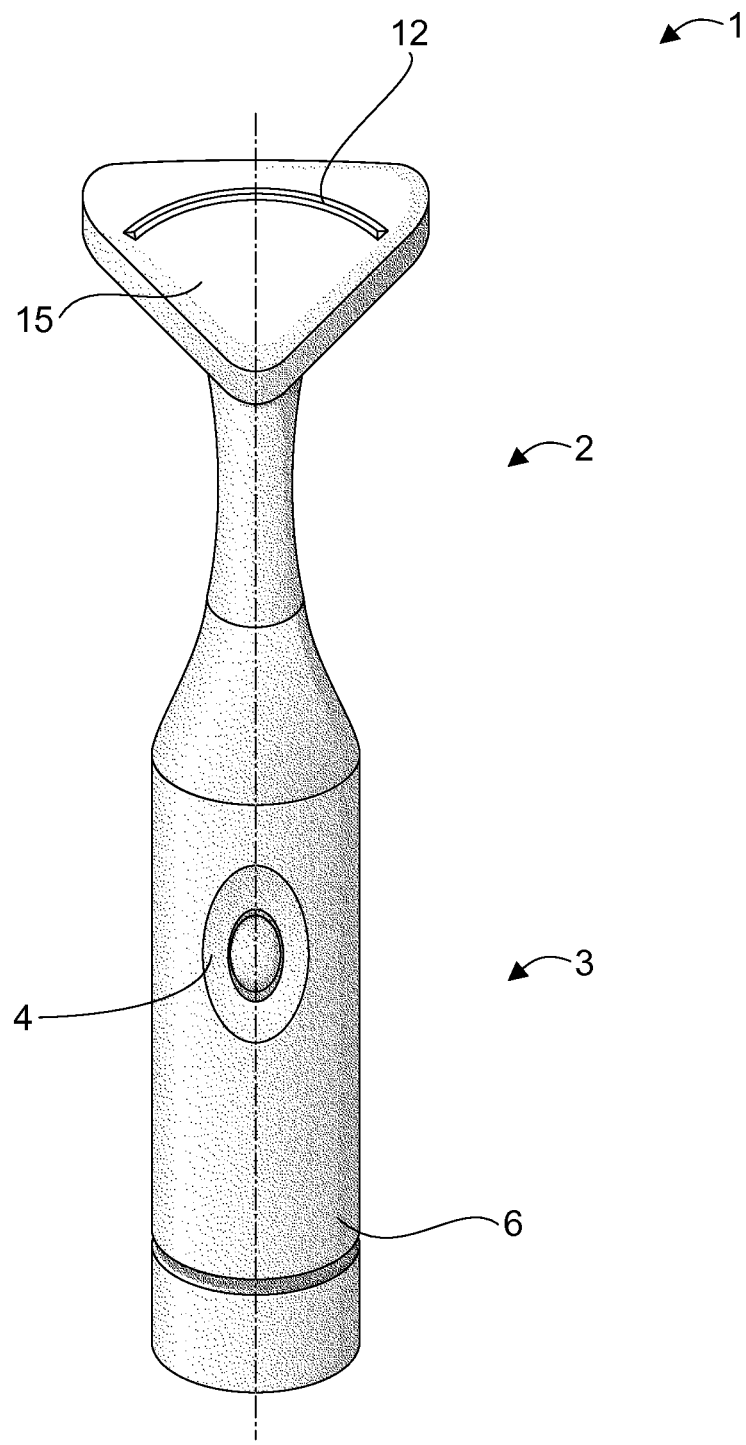
FIG. 4 is a frontal view of a third exemplary embodiment of the tongue cleaning device.
Figure 5:
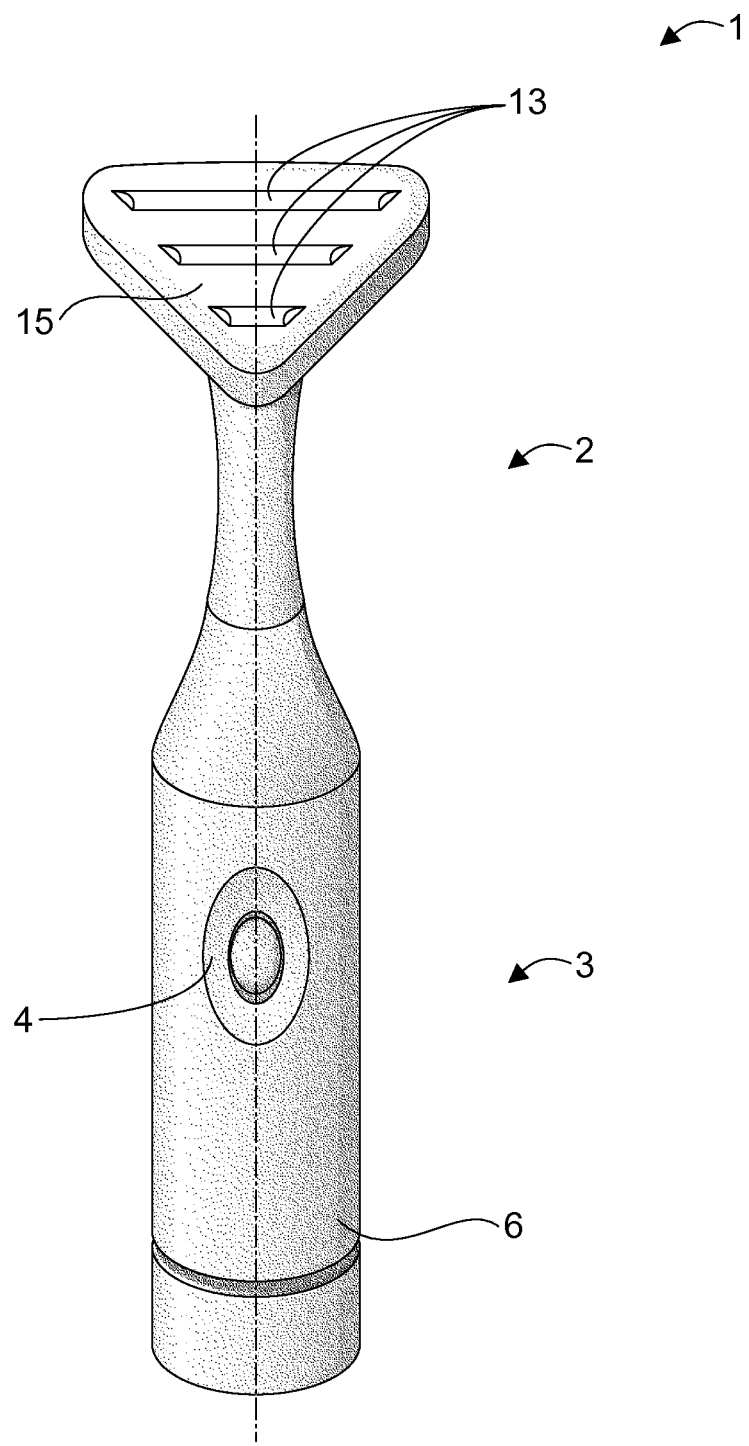
FIG. 5 is a frontal view of a fourth exemplary embodiment of a tongue cleaning device.
Figure 6:
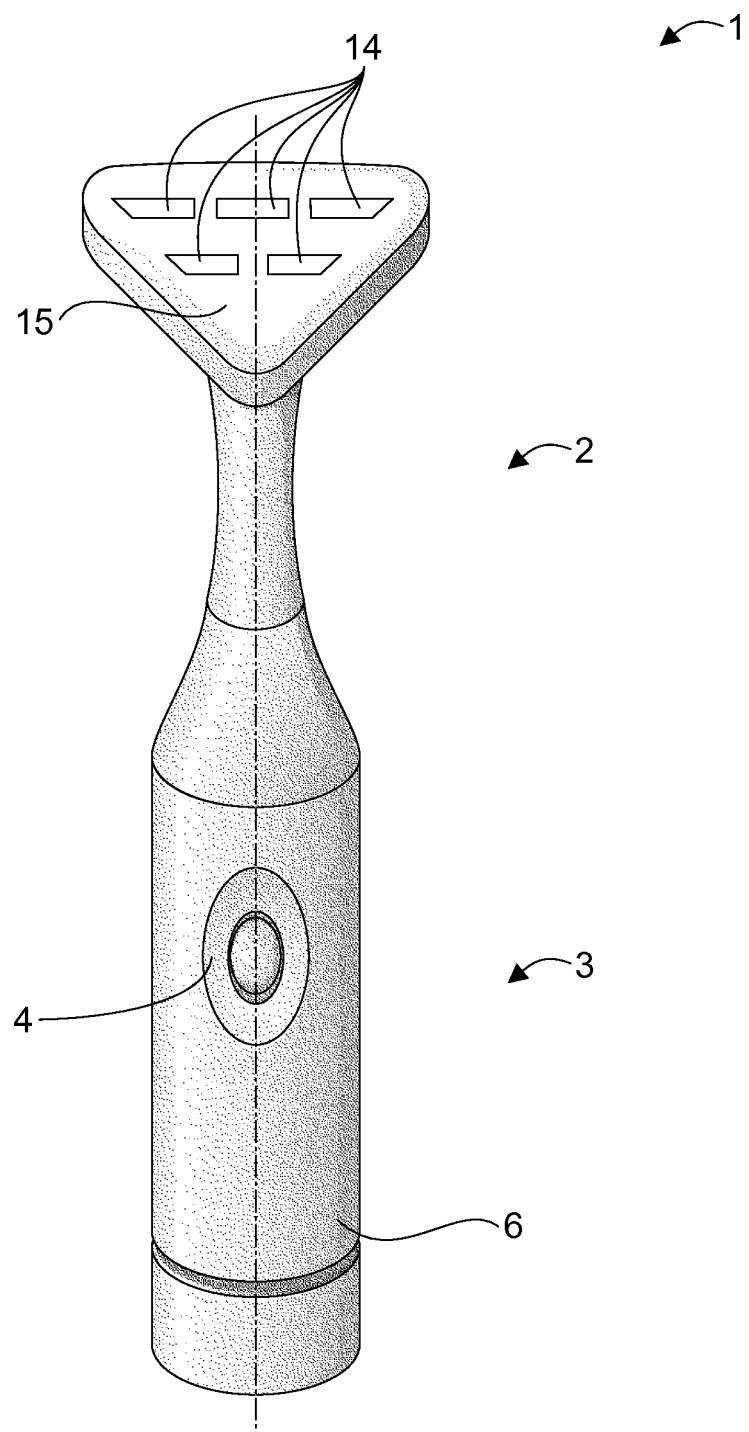
FIG. 6 is a frontal view of a fifth exemplary embodiment of tongue cleaning device.

In the third, fourth and fifth embodiments depicted in FIGS. 4 to 6, respectively, the double functionality of the tongue cleaning electrode as electrical contact surface and as mechanical scrubbing section is realized by tongue cleaning electrodes 12, 13, 14 that are forming cleaning protrusions in the form of ribs.

In order not only to apply a current, but also to allow mechanical scrubbing of the tongue the electrode 12 of the third embodiment depicted in FIG. 4 is itself shaped as a rib extending above the housing 15 of the head portion 2. The rib 12 extends essentially perpendicular to the axis of symmetry of the cylindrical housing 6 of the handle portion 3. The rib spans almost entirely over the full widths of the spoon-shaped housing 15 of the head portion 2 of the device 1. The rib 12 is also slightly curved around a centre of curvature lying on the axis of symmetry of the device between the rib 12 and the lower part of the housing 6 of the handle portion 3.

In the fourth embodiment shows in FIG. 5, the single rib 12 of the third embodiment of FIG. 4 has been replaced by a multiple set of ribs, in the shown embodiment by three ribs 13. This arrangement enhances the effect of mechanical scrubbing the tongue. In contrast, the fifth embodiment shown in FIG. 6 has five small-sized ribs 14.

Figure 7:
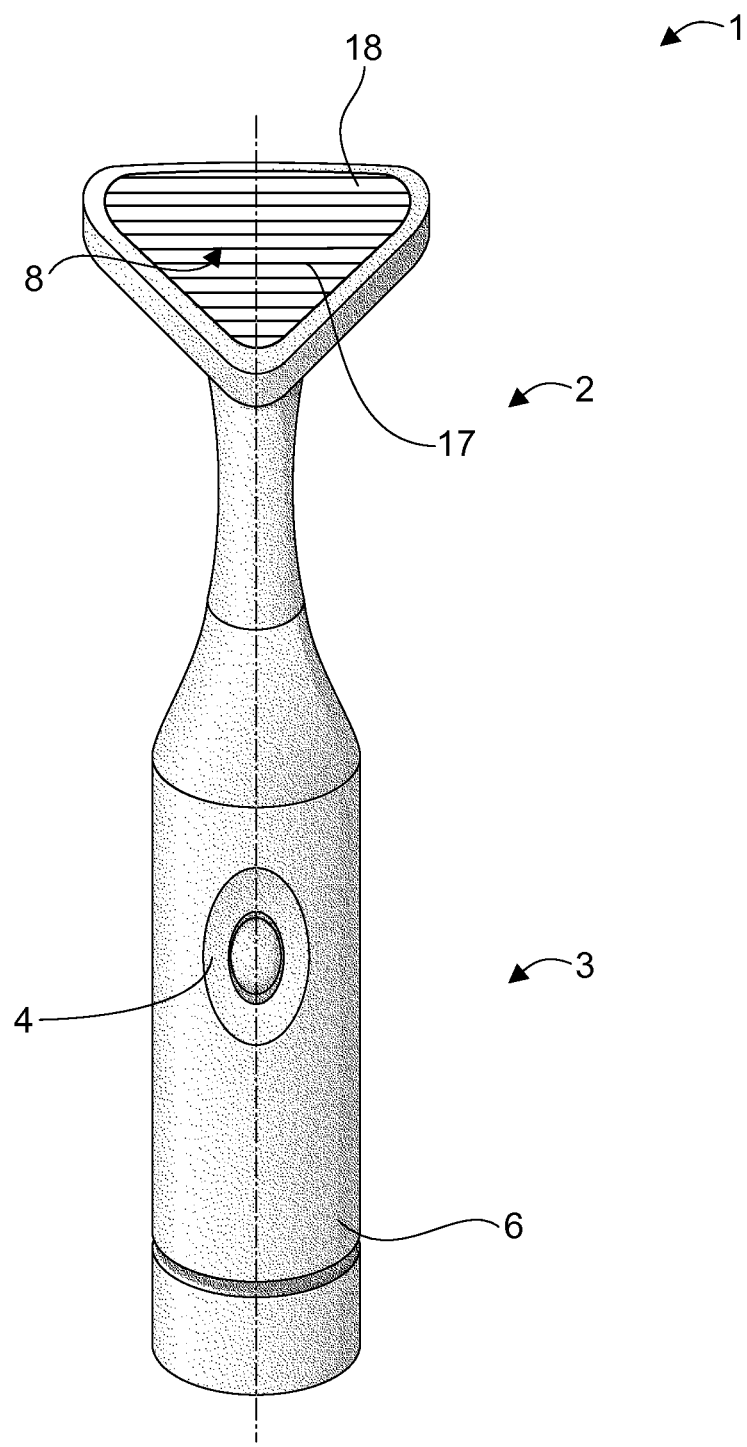
FIG. 7 is a frontal view of a sixth embodiment of the tongue cleaning device.
Figure 8:
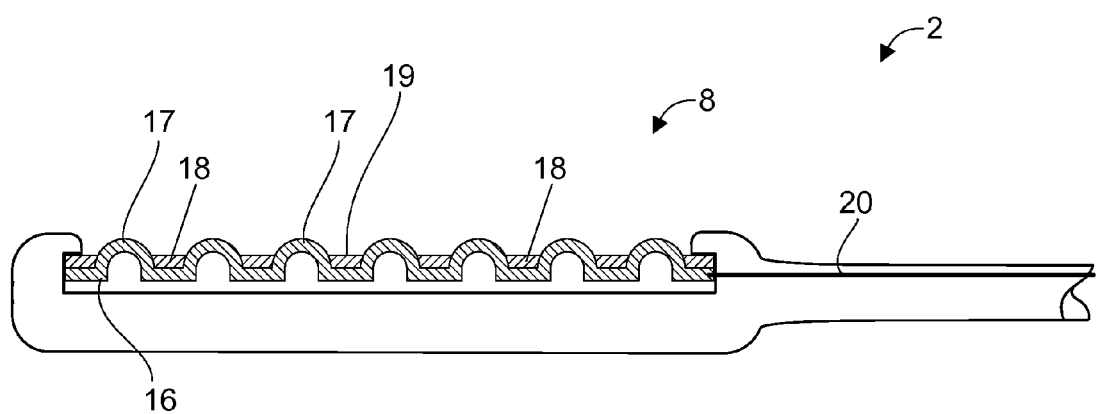
FIG. 8 is a cross-sectional view through the head portion of the tongue cleaning device of the embodiment as shown in FIG. 7.

For the sixth embodiment shown in FIGS. 7 and 8, an alternative concept is discussed to provide a tongue cleaning electrode 16 having double functionality as electrical contact and mechanical scrubbing section. Again, the area over which the tongue cleaning electrode 16 extends and the area over which the mechanical tongue cleaning section 8 extend are spatially overlapping. The tongue cleaning electrode 16 is formed by a metal sheet which has been bent in order to form a set of six cleaning protrusions in the form of metallic ribs 17 protruding from base electrode sheet. The orientation and arrangement of the metallic ribs 17 is comparable to the arrangement of the elastomeric ribs 9 shown in FIG. 1. The gap between the metallic ribs 17 has been partly filled with an electrically isolating material 18, for example, a plastics material. The isolating material 18 fills the gap between the metallic ribs 17 only partly such that the metallic ribs 17 protrude over the surface level 19 of the isolating material 18, thus enabling an effective scrubbing when moving the head portion 2 of the tongue cleaning device 1 over the user's tongue. Also shown in FIG. 8 is the electric connection for 20 coupling the tongue cleaning electrode 16 with the energy source in the handle portion 3 of the device (not shown in FIG. 8).

Figure 9:
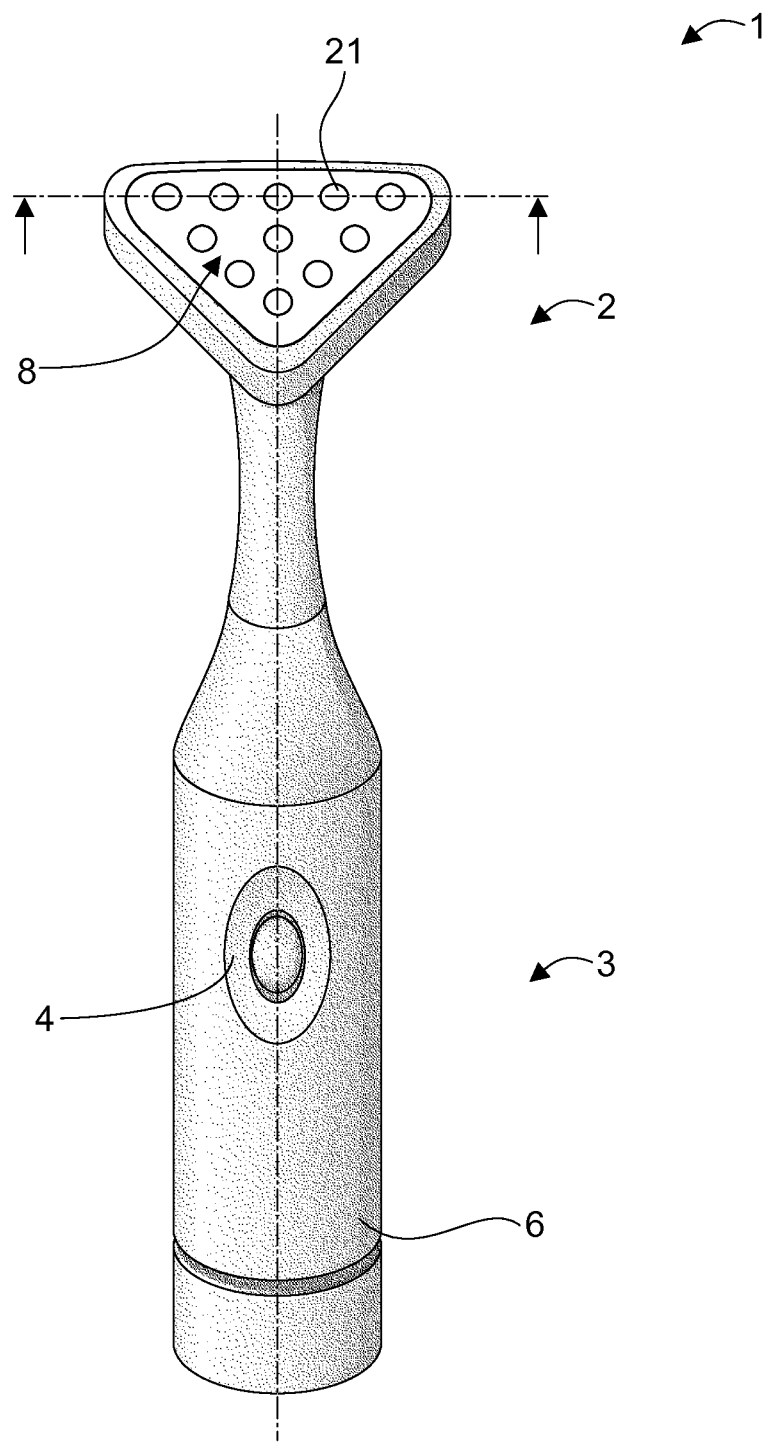
FIG. 9 is a frontal view of a seventh exemplary embodiment of the tongue cleaning device.
Figure 10:
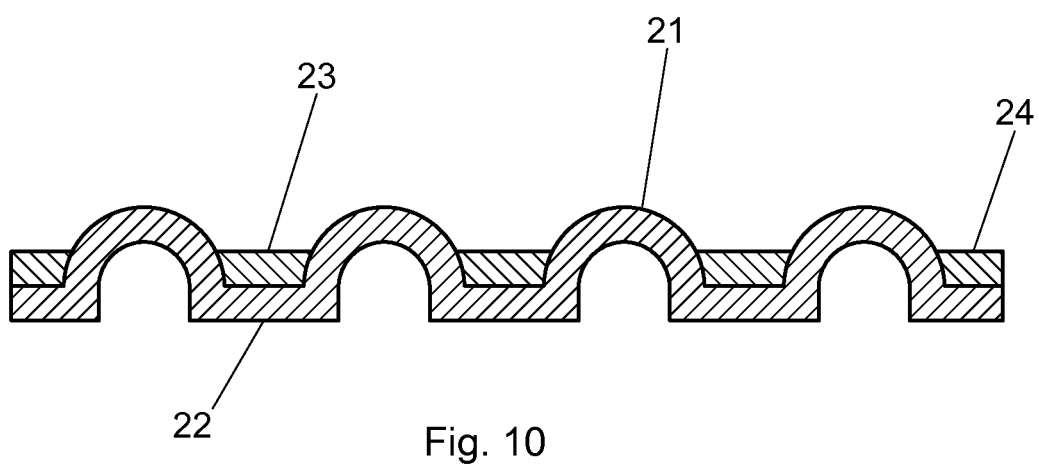
FIG. 10 is a cross-sectional view of the head portion of the tongue cleaning device as shown in FIG. 9.
Figure 11:
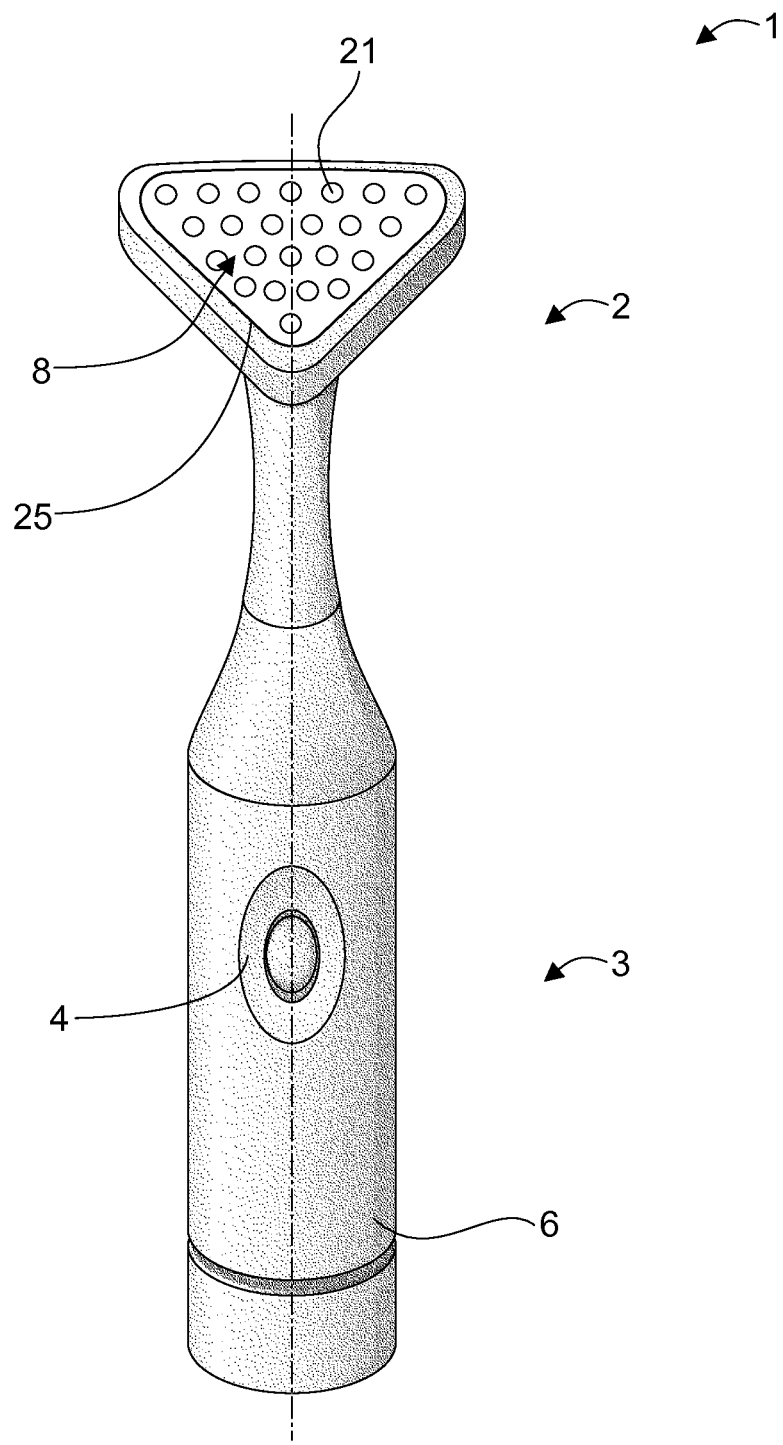
FIG. 11 is a frontal view of an eighth exemplary embodiment of a tongue cleaning device.

The seventh and eight embodiment of a tongue cleaning device as proposed shown in FIGS. 9 to 11 make use of a concept where the tongue cleaning electrode 22 is structured to have cleaning protrusions in the form of nubs 21. Again, the tongue cleaning electrode 22 fulfills a double functionality, namely to provide the electrode surface for establishing an electric contact with the user's tongue during operation and to provide a mechanical tongue cleaning section by having cleaning protrusions formed from the electrode material itself for mechanical scrubbing action. In a different embodiment, the nubs may have been attached to the tongue cleaning electrode, for example, by applying droplets of a liquid metal that solidifies and connects with the material of the tongue cleaning electrode.

FIG. 10 is a cross-sectional cut through the tongue cleaning area of the tongue cleaning device shown in FIG. 9. The tongue cleaning electrode 22 in this seventh embodiment consists of a metal foil into which a plurality of cleaning protrusions in the form of nubs 21 has been stamped such that the nubs 21 protrude from the otherwise planar sections of the electrode 22. The gaps between the individual nubs 21 again have been filled by an elastomeric plastic material 23 being electrically isolating. The nubs 21 protrude above the surface level 24 of the isolation material 23.

During operation, an electric contact between the tongue cleaning electrode 22 and the user's tongue is established by the tips of the nubs 21. Thereby the current density at the point of contact between the tongue and the structured tongue cleaning electrode 22 is enhanced, thus leading to improved cleaning action.

The seventh and eighth embodiments shown in FIGS. 9 and 11 differ from each other with respect to the dimensions and more important to the density of nubs per square centimeter.

In the embodiment depicted in FIG. 11 the nubs have a density of about 10 nubs per $cm^2$ of the overall area of the tongue cleaning electrode enclosed by the rim 25, which is equal to the working area of the mechanical tongue cleaning section of the depicted eighth embodiment. The nubs 21 of the eighth embodiment according to FIG. 11 have a height of about 1 mm measured from the surface level 24 of the insulating material 23 between the individual nubs 21 to the top of the nub 21. The widths or diameter of each of the nubs 21 measured where the nub transits into the planar material section of the electrode 21 is about 2 mm.

Figure 12:
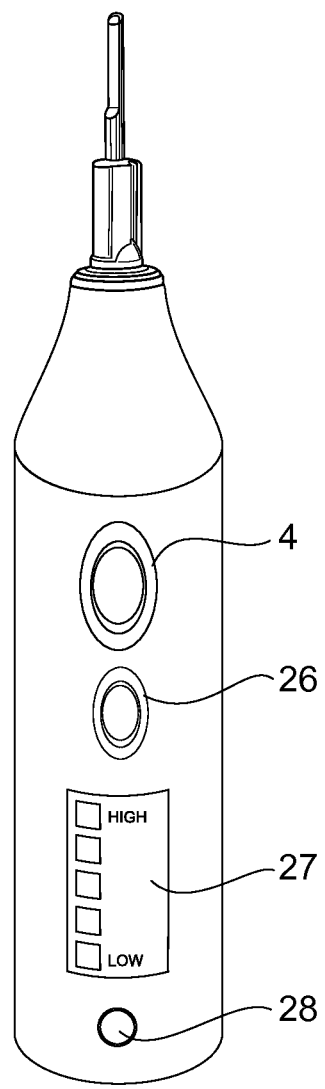
FIG. 12 is a frontal view of an alternative exemplary embodiment of a handle portion of a tongue cleaning device.

FIG. 12 shows an alternative embodiment of the handle portion of the tongue cleaning device. In this embodiment the head portion 2 and the handle portion 3 can detachably attach to each other in order to exchange the head portion. Further to the regular on/off-button 4 the handle 3 according to FIG. 12 comprises a mode setting button 26, a display 27 as well as the charge indicating light emitting diode 28.

In the shown embodiment, the mode setting button 26 is used to adopt the ionic strengths, i.e. the current used to drive the anti-bacterial agents into the tongue. The display 27 indicates the set ionic strengths and the status LED 28 indicates when the energy source needs to be recharged.

In alternative embodiments, the mode setting button 26 could be used to change between different modes of operation, for example, between an intense cleaning operation (high current) and a light refreshment operation (low current).

Figure 13:
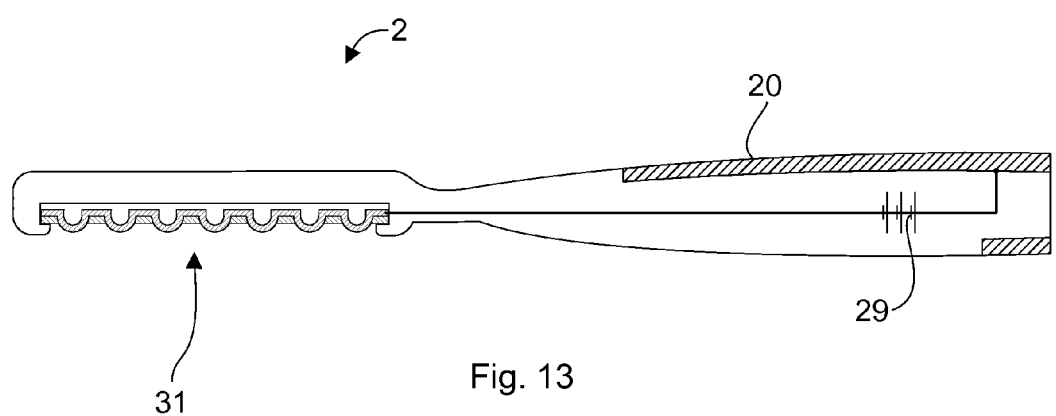
FIG. 13 is a cross-sectional view of an alternative exemplary embodiment of a head portion in accordance with the present disclosure.

FIG. 13 is a schematic cross sectional cut through an alternative embodiment of the head portion 2 forming a replacement part for a conventional handle portion. The head portion 2 may be attached to any existing handle. Accordingly the head portion 2 comprises an energy source 29, for example, one or several batteries, and a contact electrode 30 to be brought into contact with a portion of the user's body when in use (the mentioned portion may be the hand of the user or the lips, depending on the dimensions and locations of the electrodes and of the head portion). In this particular embodiment, the current flow is provided from the energy source present in the head portion to the tongue cleaning electrode 31, further though the user's body and through the contact electrode 30 on the head portion and back to the energy source 29.

In an even further embodiment, the at least one cleaning protrusion is formed like a small cylinder and the cylinder has an outer metallic cylinder surface forming the tongue cleaning electrode. The cylinder may have a plastic core. Its height dimension may be between about 0.1 mm and about 2.0 mm and its width (diameter) may be in the range of between about 0.1 mm and about 2.0 mm. In case of an embodiment with a plurality of cylindrical cleaning protrusions, each cleaning protrusion may be provided with an individual tongue cleaning electrode. The individual tongue cleaning electrodes may be electrically coupled in series or may individually be coupled to a energy source.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A head portion for a tongue cleaning device, the tongue cleaning device including an energy source and a handle portion having a contact electrode connected to the energy source, the head portion being separate from the handle portion and comprising:
a mechanical tongue cleaning section having at least one cleaning protrusion structured to be in direct mechanical contact with a tongue of a user during operation; and
at least one tongue cleaning electrode for causing a current flow into a user's body and the user's arm and tongue during operation when the tongue cleaning electrode is connected to the energy source while the user's hand contacts the contact electrode of the handle portion, the tongue cleaning electrode directly contacting the user's tongue and establishing a direct conductive connection therewith during operation, wherein the current flow has a current density of from 0.5 $\mu A/mm^2$ to 60 $\mu A/mm^2$ at the electrode surface, thereby creating an overall current flow of from 20 $\mu A$ to 80 $\mu A$ into the user's body during operation.

2. The head portion according to claim 1, wherein the mechanical tongue cleaning section and the tongue cleaning electrode are arranged such that they simultaneously contact the user's tongue during operation.

3. The head portion according to claim 1, wherein the tongue cleaning electrode is a laminar electrode.

4. The head portion according to claim 1, wherein the area over which the mechanical tongue cleaning section extends at least partly spatially overlaps with the area over which the tongue cleaning electrode extends.

5. The head portion according to claim 1, wherein the cleaning protrusion is an arc shaped rib.

6. The head portion according to claim 1, wherein the cleaning protrusion is formed of soft plastic material.

7. The head portion according to claim 1, wherein the tongue cleaning electrode forms at least a part of the mechanical tongue cleaning section.

8. The head portion according to claim 1, wherein the tongue cleaning electrode forms at least part of the cleaning protrusion.

9. The head portion according to claim 1, wherein the cleaning protrusion has a height in a range from 0.1 mm to 2 mm.

10. The head portion according to claim 1, wherein the cleaning protrusion has a width in a range from 0.1 mm to 3 mm.

11. The head portion according to claim 1, wherein the mechanical tongue cleaning section has a plurality of cleaning protrusions being arranged with a density of between 5 protrusions/$cm^2$ and 50 protrusions/$cm^2$.

12. The head portion according to claim 11, wherein the cleaning protrusions are formed by structures of the tongue cleaning electrode and are separated from each other by an electrically isolating material applied onto the tongue cleaning electrode.

13. The head portion of a tongue cleaning device according to claim 8, wherein the ratio of the area of the at least one cleaning protrusion and the overall area of the tongue cleaning electrode is in a range of between 1% and 50%.

14. The head portion according to claim 1, wherein the overall thickness of the head portion in the section where the tongue cleaning electrode is located is smaller than 15 mm.

15. The head portion according to claim 1, wherein the mechanical tongue cleaning section comprises the tongue cleaning electrode having a plurality of protrusions that directly contact a user's tongue during operation.

16. A tongue cleaning device comprising:
a head portion having a tongue cleaning section including at least one tongue cleaning electrode for enabling a current flow into a user's tongue during operation; the tongue cleaning electrode comprising at least one cleaning protrusion for directly contacting a user's tongue and establishing a direct conductive connection therewith during operation;
a handle portion separate from the head portion and including a contact electrode disposed thereon and structured and configured to contact a hand of a user during operation of the device thereby causing a current flow into a user's body and the user's arm; and an energy source housed in the handle portion;

wherein the energy source is electrically connected to the contact electrode and to the tongue cleaning electrode such that during operation of the device a current flows between the contact electrode in the handle portion and the tongue cleaning electrode in the head portion and through a user's body, and wherein the tongue cleaning electrode is structured to be in direct mechanical contact with a tongue of a user during operation and wherein the current flow has a current density of from 0.5 $\mu A/mm^2$ to 60 $\mu A/mm^2$ at the electrode surface, thereby creating an overall current flow of from 20 $\mu A$ to 80 $\mu A$ into the user's body during operation.

17. The tongue cleaning device of claim 16, wherein the tongue cleaning electrode is a laminar electrode.

18. The tongue cleaning device of claim 16, wherein the head portion comprises a mechanical tongue cleaning section having the least one cleaning protrusion.

19. The tongue cleaning device of claim 18, wherein the mechanical tongue cleaning section and the tongue cleaning electrode are arranged such that they can simultaneously get into contact with the user's tongue during operation.

20. The tongue cleaning device of claim 18, wherein an area over which the mechanical tongue cleaning section extends at least partly spatially overlaps with an area over which the tongue cleaning electrode extends.

21. The tongue cleaning device of claim 18, wherein the cleaning protrusion is an arc-shaped rib.

22. The tongue cleaning device of claim 18, wherein the cleaning protrusion is formed of soft plastic material.

23. The tongue cleaning device of claim 18, wherein the tongue cleaning electrode forms at least a part of the mechanical tongue cleaning section.

24. The tongue cleaning device of claim 18, wherein the tongue cleaning electrode forms at least part of the cleaning protrusion.

25. The tongue cleaning device of claim 18, wherein the cleaning protrusion has a height in a range from 0.1 mm to 2 mm.

26. The tongue cleaning device of claim 18, wherein the cleaning protrusion has a width in a range from 0.1 mm to 3 mm.

27. The tongue cleaning device of claim 18, wherein the mechanical tongue cleaning section has a plurality of cleaning protrusions arranged with a density of between 5 protrusions/$cm^2$ and 50 protrusions/$cm^2$.

28. The tongue cleaning device of claim 18, wherein the cleaning protrusions are formed by structures of the tongue cleaning electrode and are separated from one another by an electrically isolating material applied onto the tongue cleaning electrode.

29. The tongue cleaning device of claim 18, wherein the ratio of the area of the at least one cleaning protrusion and the overall area of the tongue cleaning electrode is in a range between 1% and 50%.

30. The tongue cleaning device of claim 18, wherein the overall thickness of the head portion in the section where the tongue cleaning electrode is located is smaller than 15 mm.

31. The tongue cleaning device of claim 18, wherein the mechanical tongue cleaning section comprises the tongue cleaning electrode having a plurality of protrusions that directly contact a user's tongue during operation.

* * * * *